Feb. 6, 1973 R. E. HAWES Plant Pat. 3,301
CARNATION PLANT
Filed June 1, 1971
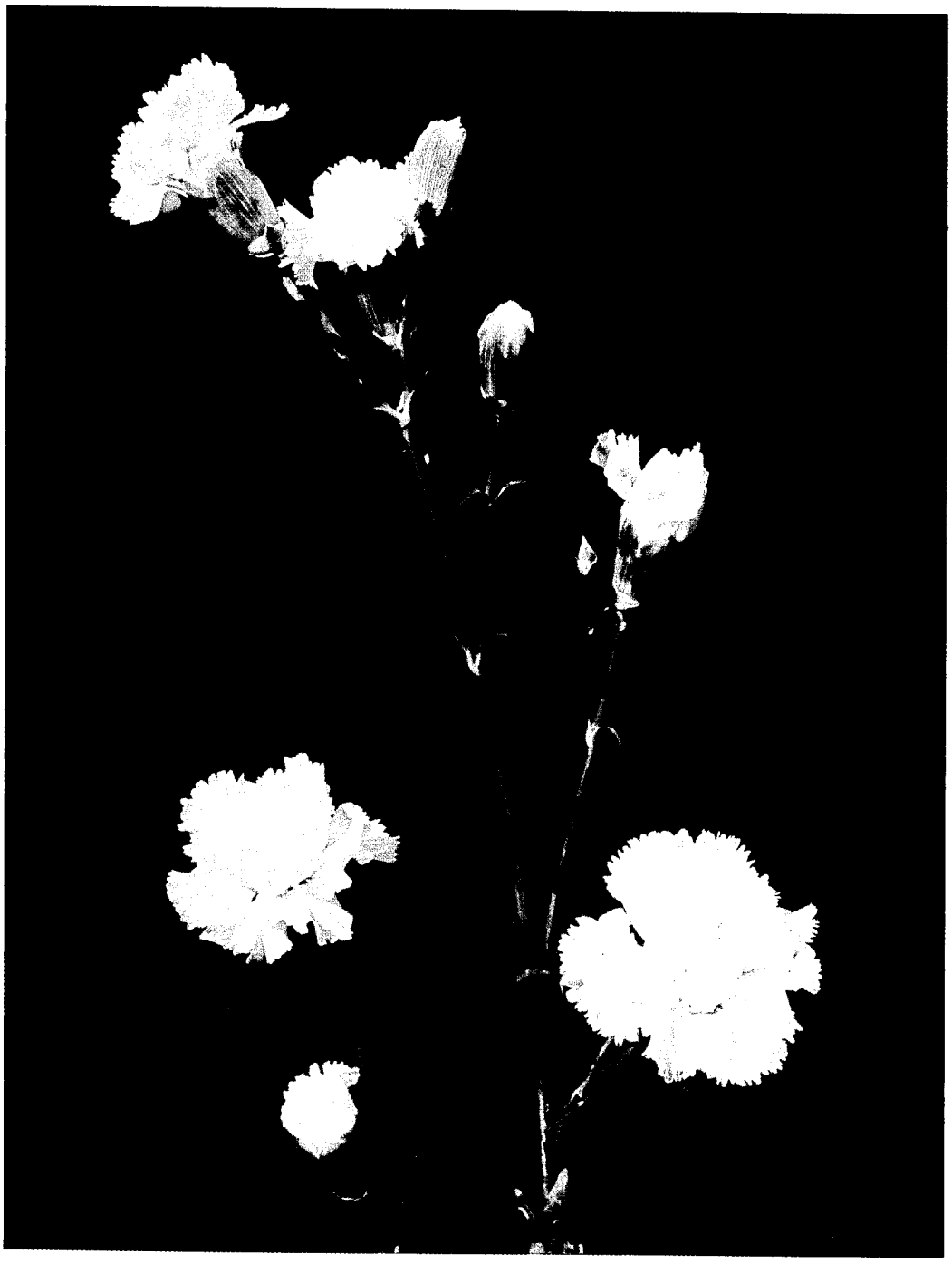

United States Patent Office

Plant Pat. 3,301
Patented Feb. 6, 1973

3,301
CARNATION PLANT

Ralph E. Hawes, 27 Highland Ave., Sudbury, Mass. 01776

Filed June 1, 1971, Ser. No. 149,089
Int. Cl. A01h *5/00*
U.S. Cl. Plt.—70 1 Claim

The present invention comprises a new and distinct cultivar of carnation plant which is a sport of the cultivar known in the United States as Twinkle, which was registered with the American Carnation Society of Philadelphia, Pa., in 1964, by Yoder Brothers, Inc. for Sal Greco. Twinkle is a sport of Chiquita, also registered with the American Carnation Society in 1964.

The new cultivar is similar in many respects to the unpatented but well-known industry standard White Elegance, having the same characteristics of:

(1) Use and culture as a miniature or spray carnation.
(2) Perpetual year-round flowering.
(3) Uniformity of cropping habit.
(4) Similar cultural requirements.

The new cultivar is distinguished from White Elegance by the following characteristics when grown under comparable conditions:

(1) More fully petalled flower, with a higher petal count of approximately 30 more per flower.
(2) The crown of the flower of the new cultivar is higher and fuller with more symmetrically placed petals.
(3) Flowers never develop hollow centers.
(4) Seven to fourteen days later response to peak flower date from comparative flowerings planted and pinched on the same date.

(5) More compact spray formation which becomes less terminal in winter under low light conditions.
(6) Stronger, shorter pedicels supporting flowers.
(7) Higher flower and bud count, averaging 1–2 more flowers and buds per stem.
(8) More ivory flower coloration.
(9) One to two days longer keeping quality under identical conditions.
(10) Under late winter and early spring conditions breaks on return crops clear lateral growth more rapidly and come into flower sooner thereby providing higher annual production per square foot per year on late season plantings.

The new cultivar was discovered in Sudbury, Mass., has been asexually reproduced by cuttings at Salinas, Calif., and has been found to retain its distinctive characteristics through successive propagations.

The following detailed description is based on observations made of the new cultivar in a greenhouse, in Salinas, Calif. The response time, blooming period, total vigor, and color may vary significantly with varying environmental conditions such as temperature, day length, and light intensity.

The accompanying drawing shows the unique characteristics of the new cultivar, the color being as nearly true as possible with color illustrations of this type. In the description which follows, color references are made to the Munsell Color Book, 1963 edition, and comparisons are made with the cultivar White Elegance. Where only a single value or description appears for the new cultivar the same value or description applies also to the comparison cultivar.

Botanical classification: *Dianthus caryophyllus*

| | Betsy | White Elegance |
|---|---|---|
| Bloom: | | |
| Type | Spray | Spray. |
| Size (diameter in inches) | 2⅛" | 2¼". |
| Average number flowers and lateral buds on spray varieties. | 6-7 | 5. |
| Petal edge | Lightly serrated | Lightly serrated. |
| Petal form | Waved or ruffled petal | Flat. |
| Petal count | Approximately 58 | Approximately 27. |
| Petal texture | | Smooth |
| Petal size: | | |
| Average length | | 1⅞-2" |
| Average width | | 1" |
| Bud shape | Ovid, fat; shorter than Elegance | Ovid, narrow. |
| Splitting tendency | | None |
| Slab tendency | | None |
| Keeping quality | 8-9 days | 7-8 days. |
| Fragrance | | Mild to none |
| Color: | | |
| Center of flower | | N9.5/white |
| Base of petals | | NGY/light yellow green |
| Inside of petals | Faint color blotches of salmon red. Blotch color 5R4/14 on N9.5/white. | Lightly flushed purple blotches, light purple 7.5P6/6 on N9.5/white. |
| Reverse of petals | | N9.5/white |
| Color stability | | Stable |
| Reproductive organs: | | |
| Stamen, anthers | 2.5Y/tan yellow | 7.5P6/6/light purple. |
| Pollen | 2.5Y8.5/6/tan | 7.5P7/2/light purple. |
| Stigma | 2 lobes, N9.5/white | 2 lobes, 7.5P6/6, light purple. |
| Styles | | N9.5/white |
| Length | | ¾" |
| Ovaries | | 5GY/light yellow green |
| Calyx: | | |
| Size: | | |
| Width | ⅝"-6" | ⅝". |
| Length | 1" | 1⅛". |
| Shape | Bell shaped | Narrow bell shaped. |
| Number of sepals | 5 | 6. |
| Stems: | | |
| Length—average, from a single pinch one-year crop. | 18" | 18". |
| Bending traits | 12 o'clock year round | 12 o'clock much of year—will weaken and bend to 3 o'clock in low light periods of winter. |
| Plant: | | |
| Form | | Erect and branching bush |
| Growth | | Vigorous, strong, sturdy, and upright |
| Height—average, from a single pinch one-year crop. | | 26"-28" |

TABLE—Continued

| | Betsy | White Elegance |
|---|---|---|
| Foliage: | | |
| Topside (color) | | 10G Y3/4, deep green |
| Underside (color) | | 10G Y5/4, steel green |
| Immature (color) | 10 G Y 3/4, deep green | 10 G Y 6/4, green. |
| Mature (color) | 10 G Y3/4, deep green | 10 G Y 3/4, deep green. |
| Length mature leaf | 5" | 4–4½". |
| Shape | Long, narrow, individual leaves which curl more than White Elegance. | Long, narrow. |
| Texture | | Glaucous |
| Displacement | | Opposite |

The table hereinbelow compares the grade data from three separate plantings of the new cultivar and the comparison cultivar, White Elegance. It will be seen from the grade data that the new cultivar provides a generally higher flower count than White Elegance, under the same growing conditions and treatment. The data also clearly shows the greater production of the new cultivar from late season plantings.

PRODUCTION AND GRADE DATA FROM PLANTINGS FLOWERED IN SALINAS, CALIF.

| Variety | Plant | Pinch | 1st cut | Peak flower | Prod. per sq. ft. | Crop, weeks | 7 grade | 5 grade | 3 grade | 1 grade | Total |
|---|---|---|---|---|---|---|---|---|---|---|---|
| Betsy | 6/06 | 6/26 | 10/13 | 11/04 | 29.2 | 48 | .26 | 42.4 | 43.5 | 13.8 | 99.96 |
| White Elegance | 6/06 | 6/26 | 10/03 | 10/24 | 29.2 | 48 | .31 | 21.7 | 58.04 | 19.9 | 99.95 |
| Betsy | 9/16 | 10/07 | 3/23 | 3/27 | 38.4 | 48 | 3.40 | 18.7 | 48.4 | 29.5 | 100.00 |
| White Elegance | 9/16 | 10/07 | 3/11 | 3/20 | 32.6 | 48 | 0 | 24.1 | 43.7 | 32.2 | 100.00 |
| Betsy | 7/15 | 8/12 | 12/01 | 1/10 | 17.0 | 38 | 0 | 16.0 | 56.0 | 28.0 | 100.00 |
| White Elegance | 7/15 | 8/12 | 11/25 | 12/28 | 14.9 | 38 | 0 | 9.0 | 62.0 | 29.0 | 100.00 |

NOTE.—Grade Data for Miniature or Spray Carnations based on American Carnation Society Standards. Key—7 grade=7+ flowers per stem; 5 grade=5+ flowers per stem; 3 grade=3+ flowers per stem; 1 grade=1+ flowers per stem.

I claim:

1. A new and distinct cultivar of carnation characterized particularly as to its uniqueness when compared to the cultivar White Elegance by its more fully petalled flower with a higher petal count of approximately 30 more per flower; a higher and fuller flower crown, with more symmetrically placed petals; flowers which never develop hollow centers; a more compact spray formation which becomes less terminal in winter under low light conditions; stronger, shorter pedicels supporting flowers; higher but count, averaging 1–2 more flowers and buds per stem; more ivory flower coloration; one to two days longer keeping quality under identical conditions; breaks on return crops clear lateral growth more rapidly and come into flower sooner under late winter and early spring conditions, thereby providing higher annual production per square foot per year on late season plantings.

No references cited.

ROBERT E. BAGWILL, Primary Examiner

UNITED STATES PATENT OFFICE

CERTIFICATE OF CORRECTION

Patent No. PP-3301 Dated February 6, 1973

Inventor(s) RALPH E. HAWES

It is certified that error appears in the above-identified patent and that said Letters Patent are hereby corrected as shown below:

Please correct the table as follows:

| | Betsy | White Elegance |
|---|---|---|
| Bloom: | | |
| Type | Spray | Spray. |
| Size (diameter in inches) | 2-1/8" | 2-1/4". |
| Average number flowers and lateral buds on spray varieties. | 6-7 | 5. |
| Petal edge | Lightly serrated | Lightly serrated. |
| Petal form | Waved or ruffled petal | Flat. |
| Petal count | Approximately 58 | Approximately 27. |
| Petal texture | Smooth | |
| Petal size: | | |
| Average length | 1-7/8 - 2" | |
| Average width | 1" | |
| Bud shape | Ovid, fat; shorter than Elegance | Ovid, narrow. |
| Splitting tendency | None | |
| Slab tendency | None | |
| Keeping quality | 8-9 days | 7-8 days. |
| Fragrance | Mild to none | |
| Color: | | |
| Center of flower | N9.5/white | |
| Base of petals | NGY/light yellow green | |
| Inside of petals | Faint color blotches of | Lightly flushed purple blotches, |

USCOMM-DC 60376-P69
★ U.S. GOVERNMENT PRINTING OFFICE : 1969 O—366-334

UNITED STATES PATENT OFFICE

CERTIFICATE OF CORRECTION

Patent No. PP-3301 Dated February 6, 1973

Inventor(s) RALPH E. HAWES

It is certified that error appears in the above-identified patent and that said Letters Patent are hereby corrected as shown below:

Please correct the table as follows: (cont.) 2

| | Betsy | White Elegance |
|---|---|---|
| | salmon red. Blotch color 5R4/14 on N9.5/white. | light purple 7.5P6/6 on N9.5/white. |
| Reverse of petals-------- | N9.5/white | |
| Color stability---------- | Stable. | |
| Reproductive organs: | | |
| Stamen, anthers---------- | 2.5Y/tan-------- yellow | 7.5P6/6/light purple. |
| Pollen---------- | 2.5Y8.5/6/tan--- | 7.5P7/2/light purple. |
| Stigma---------- | 2 lobes--------- N9.5/white | 2 lobes, 7.5P6/6 light purple. |
| Styles---------- | N9.5/white | |
| Length---------- | 3/4" | |
| Ovaries---------- | 5GY/light yellow green | |
| Calyx: | | |
| Size: | | |
| Width---------- | 5/8" - 6/8"----- | 5/8". |
| Length---------- | 1"---------- | 1-1/8". |
| Shape---------- | Bell shaped----- | Narrow bell shaped. |
| Number of sepals---------- | 5---------- | 6 |
| Stems: | | |
| Length - average, from a--- single pinch one-year crop. | 18"---------- | 18" |
| Bending traits---------- | 12 o'clock------ year round | 12 o'clock much of year - will weaken |

USCOMM-DC 60376-P69
* U.S. GOVERNMENT PRINTING OFFICE : 1969 O—366-334

UNITED STATES PATENT OFFICE

CERTIFICATE OF CORRECTION

Patent No. PP-3301 Dated February 6, 1973

Inventor(s) RALPH E. HAWES

It is certified that error appears in the above-identified patent and that said Letters Patent are hereby corrected as shown below:

Please correct the table as follows: (cont.) 3

| | Betsy | White Elegance |
|---|---|---|
| | | and bend to 3 o'clock in low light periods of winter. |
| Plant: | | |
| Form | Erect and branching bush | |
| Growth | Vigorous, strong, sturdy, and upright | |
| Height - average, from a single pinch one-year crop. | 26" - 28" | |
| Foliage: | | |
| Topside (color) | 10GY3/4 deep green | |
| Underside (color) | 10GY5/4 steel green | |
| Immatrue (color) | 10GY3/4 deep green | 10GY6/4, green. |
| Mature (color) | 10GY3/4 deep green | 10GY3/4 deep green. |
| Length mature leaf | 5" | 4 - 4-1/2" |
| Shape | Long, narrow, individual leaves which curl more than White Elegance | Long, narrow. |
| Texture | Glaucous | |
| Displacement | Opposite | |

Signed and sealed this 6th day of November 1973.

(SEAL)
Attest:

EDWARD M.FLETCHER,JR.
Attesting Officer

RENE D. TEGTMEYER
Acting Commissioner of Patents